(12) United States Patent
Satoh

(10) Patent No.: US 11,465,788 B2
(45) Date of Patent: Oct. 11, 2022

(54) METHOD OF MANUFACTURING PACKAGE STRUCTURE

(71) Applicant: ZEON CORPORATION, Tokyo (JP)

(72) Inventor: Yoshitaka Satoh, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 874 days.

(21) Appl. No.: 16/335,375

(22) PCT Filed: Sep. 19, 2017

(86) PCT No.: PCT/JP2017/033711
§ 371 (c)(1),
(2) Date: Mar. 21, 2019

(87) PCT Pub. No.: WO2018/061865
PCT Pub. Date: Apr. 5, 2018

(65) Prior Publication Data
US 2019/0276170 A1    Sep. 12, 2019

(30) Foreign Application Priority Data

Sep. 28, 2016    (JP) .............................. JP2016-189632

(51) Int. Cl.
| | | |
|---|---|---|
| *B65B 11/50* | (2006.01) | |
| *A61F 13/00* | (2006.01) | |
| *B65B 55/02* | (2006.01) | |
| *A61F 15/00* | (2006.01) | |
| *B65B 55/08* | (2006.01) | |
| *C08J 3/09* | (2006.01) | |
| *C08L 9/10* | (2006.01) | |
| *A61F 13/02* | (2006.01) | |
| *C09J 109/00* | (2006.01) | |
| *C09J 193/04* | (2006.01) | |
| *C09J 109/08* | (2006.01) | |
| *A61B 50/30* | (2016.01) | |

(52) U.S. Cl.
CPC .............. *B65B 11/50* (2013.01); *A61B 50/30* (2016.02); *A61F 13/00076* (2013.01); *A61F 13/02* (2013.01); *A61F 13/0276* (2013.01); *A61F 15/001* (2013.01); *A61F 15/002* (2013.01); *B65B 55/02* (2013.01); *B65B 55/08* (2013.01); *C08J 3/092* (2013.01); *C08L 9/10* (2013.01); *C09J 109/00* (2013.01); *C09J 109/08* (2013.01); *C09J 193/04* (2013.01); *C08J 2309/10* (2013.01)

(58) Field of Classification Search
CPC .......................... B65B 11/50; A61F 13/00076
See application file for complete search history.

(56) References Cited

U.S. PATENT DOCUMENTS

| | | | |
|---|---|---|---|
| 4,393,080 A | 7/1983 | Pawelchak et al. | |
| 4,855,335 A | 8/1989 | Neperud | |
| 5,939,339 A * | 8/1999 | Delmore et al. ..... | A61F 13/0273 602/76 |
| 6,099,682 A * | 8/2000 | Krampe et al. ..... | B65D 75/5855 156/289 |
| 8,096,417 B2* | 1/2012 | Iwao et al. ............ | A61F 15/001 206/484 |
| 2004/0120849 A1 | 6/2004 | Stewart et al. | |
| 2004/0241246 A1 | 12/2004 | Lipman | |
| 2005/0095436 A1* | 5/2005 | Story .................. | C09J 123/0853 428/521 |
| 2011/0306677 A1* | 12/2011 | Kataoka ................ | C09J 109/00 523/111 |
| 2012/0006710 A1 | 1/2012 | Hatanaka et al. | |
| 2013/0012859 A1* | 1/2013 | Krohn ............... | A61F 13/00076 604/385.01 |
| 2013/0310777 A1 | 11/2013 | Nishimura et al. | |
| 2014/0158571 A1* | 6/2014 | Matsuoka et al. .......................... | A61F 13/00076 206/438 |

FOREIGN PATENT DOCUMENTS

| | | | | |
|---|---|---|---|---|
| CN | 103169687 A | * | 6/2013 | ......... A61F 13/0259 |
| CN | 103338757 A | | 10/2013 | |
| CN | 104411796 A | | 3/2015 | |
| EP | 0 528 191 A1 | | 2/1993 | |
| JP | 2003325575 A | * | 11/2003 | ....... A61F 13/00076 |
| WO | 2010/110130 A1 | | 9/2010 | |

OTHER PUBLICATIONS

Mar. 5, 2021 Office Action issued in European Patent Application No. 17855820.1.
Sep. 15, 2021 Office Action issued in Chinese Patent Application No. 201780055098.2.
Qian, Miaogen, "Modern Surface Engineering," Shanghai Jiaotong University Press, p. 373, 2012.
Nov. 28, 2017 Search Report issued in International Patent Application No. PCT/JP2017/033711.

* cited by examiner

*Primary Examiner* — Stephen F. Gerrity
(74) *Attorney, Agent, or Firm* — Oliff PLC

(57) ABSTRACT

A method of producing a packaging structure, including the steps: coating at least one surface of a first sheet base material and/or a second sheet base material with a synthetic polyisoprene latex having a weight average molecular weight of 500,000 -5,000,000 and/or a styrene-isoprene-styrene block copolymer having a weight average molecular weight of 100,000-300,000, sandwiching an article to be packaged in a state wherein the first and second sheet base material are in contact with each other via a latex coated surface formed on the first and/or second sheet base material to thereby obtain a laminated body, pressing a portion where at least the first and second sheet base material of the laminated body are in contact with each other via the latex coated surface at a temperature of 100° C. or less to thereby obtain a pressed laminated body, and performing a sterilization treatment on the pressed laminated body.

6 Claims, No Drawings

METHOD OF MANUFACTURING PACKAGE STRUCTURE

TECHNICAL FIELD

The present invention relates to a method of producing a packaging structure famed by packaging an article to be packaged by a pair of sheet base materials, and more particularly, to a method of producing a packaging structure which can adhere sheet base materials to each other at a suitable adhesive strength, and in which occurrence of stringiness at the adhered portion of the sheet base materials is effectively prevented.

BACKGROUND ART

Conventionally, a packaging structure famed by packaging an article to be packaged, such as an adhesive plaster, by a pair of sheet base materials, is known. As such a packaging structure, for example, Patent Document 1 discloses a packaging structure that accommodates an adhesive plaster between a pair of sheet base materials on which a cold seal layer composed of a mixture of rubber and acrylic resin is famed. This packaging structure is obtained by adhering the cold seal layers of the sheet base materials together by cold pressing, which enables the sheet base materials to be easily peeled from the article to be packaged while the sheet base materials are still adhered together.

RELATED ART

Patent Documents

Patent Document 1: International Publication No. WO 2010/110130

SUMMARY OF THE INVENTION

Problem to be Solved by the Invention

On the other hand, the packaging structure obtained by the technique of Patent Document 1 suffers from a problem in that, when attempting to secure adhesive strength between the sheet base materials, during peeling of the sheet base material from the packaging structure to remove the article to be packaged, stringiness (a phenomenon in which a part of one of the cold seal layers remains adhered to the other cold seal layer when peeling the sheet base materials, and extends in a string-like form) occurs at the adhered portion between the sheet base materials.

The present invention has been made in view of such circumstances, and it is an object of the present invention to provide a method of producing a packaging structure that is capable of adhering the sheet base materials for packaging an article to be packaged at a suitable adhesive strength, and that effectively prevents stringiness (a phenomenon in which a part of the adhered portion of one of the sheet base materials remains adhered to the adhered portion of the other sheet base material when peeling the sheet base materials, and extends in a string-like form) at the adhered portion between the sheet base materials.

Means for Solving the Problem

The present inventors discovered that the above-mentioned object could be achieved by using a pair of sheet base materials coated with a latex of a synthetic polyisoprene having a weight average molecular weight within a predetermined range and/or a styrene-isoprene-styrene block copolymer to obtain a laminated body in which an article to be packaged is sandwiched so that at least the part of a latex coated surface of each sheet base material are in direct contact with each other, then pressing the portions where at least the sheet base materials of the laminated body are in direct contact at a temperature of 100° C. or less to obtain a pressed laminated body, and performing a sterilization treatment on the pressed laminated body, thereby completing the present invention.

Specifically, according to the present invention, provided is a method of producing a packaging structure, comprising a coating step of coating at least one surface of a first sheet base material and/or a second sheet base material with a latex of a synthetic polyisoprene having a weight average molecular weight of 500,000 to 5,000,000 and/or a styrene-isoprene-styrene block copolymer having a weight average molecular weight of 100,000 to 300,000, a lamination step of sandwiching an article to be packaged between the first sheet base material and the second sheet base material in a state in which at least a part of the latex coated surface of the first sheet base material and at least a part of the latex coated surface of the second sheet base material are in direct contact with each other to thereby obtain a laminated body, a pressing step of pressing a portion where at least the first sheet base material and the second sheet base material of the laminated body are in direct contact with each other at a temperature of 100° C. or less to thereby obtain a pressed laminated body, and a sterilizing step of performing a sterilization treatment on the pressed laminated body.

In the present invention, it is preferable that the latex contain rosinate.

In the present invention, it is preferable that the latex have a solid content concentration of 10 to 70% by weight.

In the present invention, it is preferable that the article to be packaged is an adhesive plaster.

Effects of Invention

According to the present invention, there can be provided a method of producing a packaging structure which can adhere sheet base materials packaging an article to be packaged to each other at a suitable adhesive strength, and in which occurrence of stringiness at the adhered portion of the sheet base materials is effectively prevented.

DESCRIPTION OF EMBODIMENTS

A method of producing a packaging structure of the present invention comprises:

a coating step of coating at least one surface of a first sheet base material and/or a second sheet base material with a latex of a synthetic polyisoprene having a weight average molecular weight of 500,000 to 5,000,000 and/or a styrene-isoprene-styrene block copolymer having a weight average molecular weight of 100,000 to 300,000;

a lamination step of sandwiching an article to be packaged between the first sheet base material and the second sheet base material in a state in which at least a part of a latex coated surface of the first sheet base material and at least a part of a latex coated surface of the second sheet base material are in direct contact with each other to thereby obtain a laminated body;

a pressing step of pressing a portion where at least the first sheet base material and the second sheet base material of the laminated body are in direct contact with each other at a temperature of 100° C. or less to thereby obtain a pressed laminated body; and a sterilizing step of performing a sterilization treatment on the pressed laminated body.

Synthetic Polyisoprene Latex

First, the synthetic polyisoprene latex used in the production method of the present invention will be described.

The synthetic polyisoprene latex used in the present invention is a synthetic polyisoprene latex obtained by polymerizing isoprene. The synthetic polyisoprene included in the synthetic polyisoprene latex used in the present invention may be a homopolymer of isoprene or a copolymer of isoprene and another ethylenically unsaturated monomer copolymerizable therewith. From the viewpoint that the adhesive strength between the sheet base materials of the obtained packaging structure can be made more suitable, the content of the isoprene unit in the synthetic polyisoprene is, based on all monomer units, preferably 70% by weight or more, more preferably 90% by weight or more, even more preferably 95% by weight or more, and particularly preferably 100% by weight (homopolymer of isoprene).

Examples of other ethylenically unsaturated monomers copolymerizable with isoprene include: conjugated diene monomers other than isoprene, such as butadiene, chloroprene, and 1,3-pentadiene; ethylenically unsaturated nitrile monomers such as acrylonitrile, methacrylonitrile, fumaronitrile, and a -chloroacrylonitrile; vinyl aromatic monomers such as styrene and alkylstyrene; ethylenically unsaturated carboxylic acid ester monomers such as methyl (meth)acrylate (meaning "methyl acrylate and/or methyl methacrylate"; hereinafter, this also applies for ethyl (meth)acrylate etc.), ethyl (meth)acrylate, butyl (meth)acrylate, and 2-ethylhexyl (meth)acrylate; and the like. These ethylenically unsaturated monomers copolymerizable with isoprene may be used singly or in combination of two or more kinds.

The synthetic polyisoprene can be obtained by a conventionally known method, for example, a method in which isoprene and an optionally-used another copolymerizable ethylenically unsaturated monomer are subjected to solution polymerization in an inert polymerization solvent using a polymerization catalyst. The polymer solution of the synthetic polyisoprene obtained by solution polymerization may be used as is in the production of the synthetic polyisoprene latex, but may also be used by collecting solid synthetic polyisoprene from the polymer solution and then dissolving in an organic solvent for use in the production of the synthetic polyisoprene latex.

At this time, impurities such as a residue of the polymerization catalyst remaining in the polymer solution after synthesis may be removed. In addition, an anti-aging agent (described later) may be added to the solution during or after polymerization. Commercially available solid synthetic polyisoprene can also be used.

Examples of the polymerization catalyst for obtaining the synthetic polyisoprene include, but are not particularly limited to, trivalent and/or tetravalent transition metal compounds, such as a Ziegler type polymerization catalyst composed of trialkylaluminum-titanium tetrachloride; alkyllithium polymerization catalysts such as n-butyllithium and sec-butyllithium; and the like. Among these, from the viewpoint that the adhesive strength between the sheet base materials of packaging structure obtained can be made more suitable, a trivalent and/or tetravalent transition metal compound is preferable, and a Ziegler type polymerization catalyst composed of trialkylaluminum-titanium tetrachloride is particularly preferable.

There are four kinds of isoprene units in synthetic polyisoprene, which are, according to the bonding state of isoprene, a cis bond unit, a trans bond unit, a 1,2-vinyl bond unit, and a 3,4-vinyl bond unit. From the viewpoint that the adhesive strength between the sheet base materials of the obtained packaging structure can be made more suitable, the content ratio of the cis bond units in the isoprene unit included in the synthetic polyisoprene is, based on all isoprene units, preferably 70% by weight or more, more preferably 90% by weight or more, and even more preferably 95% by weight or more.

The weight average molecular weight of the synthetic polyisoprene may be, in terms of standard polystyrene as determined by gel permeation chromatography analysis, 500,000 to 5,000,000, preferably 700,000 to 3,000,000, more preferably 800,000 to 2,500,000, and even more preferably 900,000 to 2,000,000. If the weight average molecular weight of the synthetic polyisoprene is too large, the effect of an improvement in the adhesiveness of the synthetic polyisoprene by a sterilization treatment (described later) is insufficient, and as a result, the adhesive strength between the sheet base materials of the obtained packaging structure is reduced, and the sheet base materials may peel from each other. On the other hand, if the weight average molecular weight of the synthetic polyisoprene is too small, the effect of an improvement in the adhesiveness of the synthetic polyisoprene by the sterilization treatment (described later) becomes excessive, and as a result, the viscosity of the synthetic polyisoprene becomes too high, so that when peeling the sheet base materials in order to remove the article to be packaged from the packaging structure, stringiness may be produced at the adhered portion between the sheet base materials.

The polymer-Mooney viscosity (ML 1+4, 100° C.) of the synthetic polyisoprene is preferably 50 to 80, more preferably 60 to 80, and even more preferably 70 to 80.

In the present invention, it is preferable to introduce a polar group into the synthetic polyisoprene produced in this way. Examples of the polar group include, but are not particularly limited to, a carboxyl group, a hydroxyl group, an epoxy group, and the like. Among these, a carboxyl group is preferable. For example, in the case of introducing a carboxyl group into the synthetic polyisoprene, examples of the method to carry this out include a method of introducing a carboxyl group by graft polymerizing in aqueous phase a monomer having a carboxyl group to a synthetic polyisoprene. In this case, in order to perform graft polymerization in aqueous phase of the monomer having a carboxyl group, it is preferable to use a synthetic polyisoprene latex.

The content ratio of the polar group in the synthetic polyisoprene is the content ratio of the monomer unit having a polar group in the synthetic polyisoprene. This content ratio is, based on all monomer units, preferably 0.1 to 5% by weight, more preferably 0.5 to 5% by weight, and even more preferably 0.8 to 5% by weight. Note that, in the case where a polar group is introduced by copolymerizing a monomer having a polar group with isoprene as another ethylenically unsaturated monomer copolymerizable with isoprene, the content ratio of the monomer unit having a polar group in the synthetic polyisoprene may include, in addition to the amount of the monomer unit having a polar group introduced into the synthetic polyisoprene by graft polymerization or the like as described above, the amount of the monomer having such a polar group.

Examples of the method of obtaining a synthetic polyisoprene latex include: (1) a method of a producing the synthetic polyisoprene latex by emulsifying in water a solution or fine suspension of synthetic polyisoprene dissolved or finely dispersed in an organic solvent in the presence of an anionic surfactant; and (2) a method of producing the synthetic polyisoprene latex directly by subjecting isoprene alone or a mixture of isoprene and an ethylenic unsaturated monomer copolymerizable therewith to emulsion polymerization or suspension polymerization in the presence of an to anionic surfactant. However, from the viewpoint that a synthetic polyisoprene having a high ratio of cis bond units in the isoprene unit can be used and the viewpoint that the adhesive strength between the sheet base materials of the obtained packaging structure can be made more suitable, production method (1) above is preferable.

Examples of the organic solvent used in the production method (1) above include: aromatic hydrocarbon solvents such as benzene, toluene, and xylene; alicyclic hydrocarbon solvents such as cyclopentane, cyclopentene, cyclohexane, and cyclohexene; aliphatic hydrocarbon solvents such as pentane, hexane, and heptane; halogenated hydrocarbon solvents such as methylene chloride, chloroform, and ethylene dichloride; and the like. Among these, an alicyclic hydrocarbon solvent is preferable, and cyclohexane is particularly preferable.

The used amount of the organic solvent used is, based on 100 parts by weight of the synthetic polyisoprene, preferably 2,000 parts by weight or less, more preferably 20 to 1,500 parts by weight, and even more preferably 500 to 1,500 parts by weight.

Examples of the anionic surfactant used in the production method (1) above include: fatty acid salts such as sodium laurate, potassium myristate, sodium palmitate, potassium oleate, sodium linolenate, sodium rosinate, and potassium rosinate; alkylbenzene sulfonates such as sodium dodecylbenzenesulfonate, potassium dodecylbenzenesulfonate, sodium decylbenzenesulfonate, potassium decylbenzenesulfonate, sodium cetylbenzenesulfonate, and potassium cetylbenzenesulfonate; alkyl sulfosuccinates such as sodium di(2-ethylhexyl)sulfosuccinate, potassium di(2-ethylhexyl) sulfosuccinate, and sodium dioctylsulfosuccinate; alkyl sulfates such as sodium lauryl sulfate and potassium lauryl sulfate; polyoxyethylene alkyl ether sulfates such as sodium polyoxyethylene lauryl ether sulfate and potassium polyoxyethylene lauryl ether sulfate; monoalkyl phosphates such as sodium lauryl phosphate and potassium lauryl phosphate; and the like.

Among these anionic surfactants, fatty acid salts, alkylbenzene sulfonates, alkyl sulfosuccinates, alkyl sulfates, and polyoxyethylene alkyl ether sulfates are preferable, fatty acid salts and alkylbenzene sulfonates are more preferable, fatty acid salts are even more preferable, and rosinates such as sodium rosinate and potassium rosinate are particularly preferable. When these anionic surfactants are used, the obtained synthetic polyisoprene latex contains an anionic surfactant. According to the present invention, by using a rosinate as the anionic surfactant, the obtained synthetic polyisoprene latex contains a rosinate. In such a case, the rosinate acts as a pressure-sensitive adhesive, which enables the adhesive strength between the sheet base materials of the obtained packaging structure to be more suitable.

When the synthetic polyisoprene latex contains a rosinate, the content ratio of the rosinate is, based on 100 parts by weight of the synthetic polyisoprene, preferably 0.5 to 4 parts by weight, more preferably 0.8 to 4 parts by weight, and even more preferably 1 to 4 parts by weight. When the content ratio of the rosinate is within the above range, the adhesive strength between the sheet base materials of the obtained packaging structure can be made more suitable by the action of the rosinate as a pressure-sensitive adhesive.

Further, from the perspective of enabling polymerization catalyst (in particular, aluminum and titanium) remaining in trace amounts derived from the synthetic polyisoprene to be removed more efficiently, and suppressing generation of aggregates during production of the latex composition, it is preferable to use at least one salt selected from the group consisting of alkylbenzene sulfonates, alkyl sulfosuccinates, alkyl sulfates, and polyoxyethylene alkyl ether sulfates in combination with a fatty acid salt, and it is particularly preferable to use an alkylbenzene sulfonate in combination with a fatty acid salt. Here, as the fatty acid salt, sodium rosinate and potassium rosinate are preferable, and as the alkylbenzene sulfonate, sodium dodecylbenzenesulfonate and potassium dodecylbenzenesulfonate are preferable. These surfactants may be used singly or in combination of two or more kinds.

As described above, by using at least one salt selected from the group consisting of alkylbenzene sulfonates, alkyl sulfosuccinates, alkyl sulfates, and polyoxyethylene alkyl ether sulfates in combination with a fatty acid salt, the obtained synthetic polyisoprene latex contains at least one salt selected from alkylbenzene sulfonates, alkyl sulfosuccinates, alkyl sulfates, and polyoxyethylene alkyl ether sulfates, and a fatty acid salt.

In the production method (1) above, a surfactant other than an anionic surfactant may also be used in combination. Examples of such a surfactant other than an anionic surfactant include copolymerizable surfactants such as a sulfoester of an $\alpha,\beta$-unsaturated carboxylic acid, a sulfate ester of an $\alpha,\beta$-unsaturated carboxylic acid, and sulfoalkylaryl ether.

Further, nonionic surfactants such as polyoxyethylene alkyl ether, polyoxyethylene alkylphenol ether, polyoxyethylene alkyl ester, and polyoxyethylene sorbitan alkyl ester may also be used in combination.

The used amount of the anionic surfactant used in the production method (1) above is, based on 100 parts by weight of the synthetic polyisoprene, preferably 0.1 to 50 parts by weight, and more preferably 0.5 to 30 parts by weight. In the case where two or more surfactants are used, it is preferable that the total amount of those surfactants be in the above range. That is, for example, when at least one kind selected from alkylbenzene sulfonates, alkyl sulfosuccinates, alkyl sulfates, and polyoxyethylene alkyl ether sulfates is used in combination with a fatty acid salt, it is preferable to set the total used amount of these in the above range. When the used amount of the anionic surfactant is within the above range, the occurrence of aggregates during emulsification can be suppressed.

When at least one kind selected from alkylbenzene sulfonates, alkyl sulfosuccinates, alkyl sulfates, and polyoxyethylene alkyl ether sulfates is used as an anionic surfactant in combination with a fatty acid salt, it is preferable to set the weight ratio of the "fatty acid salt" : "total of at least one surfactant selected from alkylbenzene sulfonates, alkyl sulfosuccinates, alkyl sulfates, and polyoxyethylene alkyl ether sulfates" in the range of 1:1 to 10:1, and more preferably in the range of 1:1 to 7:1. When the usage ratio of the at least one surfactant selected from alkylbenzene sulfonates, alkyl sulfosuccinates, alkyl sulfates, and polyoxyethylene alkyl ether sulfates is too large, foaming may be more severe when handling the synthetic polyisoprene, and as a result, an operation such as leaving to stand for a long time or adding an antifoaming agent is required, which may lead to a deterioration in workability and increased costs.

The amount of water used in the production method (1) above is, based on 100 parts by weight of the synthetic polyisoprene organic solvent solution, preferably 10 to 1,000 parts by weight, more preferably 30 to 500 parts by weight, and most preferably 50 to 100 parts by weight. Examples of the kind of water to be used include hard water, soft water, ion exchanged water, distilled water, zeolite water, and the like. Soft water, ion exchanged water, and distilled water are preferable.

The apparatus for emulsifying the solution or fine suspension of the synthetic polyisoprene dissolved or finely dispersed in an organic solvent in water in the presence of an anionic surfactant is not particularly limited, and any apparatus generally commercially available as an emulsifying machine or dispersing machine can be used. The method of adding the anionic surfactant to the solution or fine suspension of the synthetic polyisoprene is not particularly limited. The anionic surfactant may be added in advance to either or both of a solution or a fine suspension of water or synthetic polyisoprene, or may be added to the emulsion during the emulsification operation, and may be added all at once or divided into several additions.

Examples of the emulsifying apparatus include a batch type emulsifier such as trade name "Homogenizer" (manufactured by IKA), trade name "Polytron" (manufactured by Kinematica), or trade name "TK Auto Homo Mixer" (manufactured by Tokushu Kika Kogyo); a continuous emulsifier such as trade name "TK Pipeline Homo Mixer" (manufactured by Tokushu Kika Kogyo), trade name "Colloid Mill" (manufactured by Shinko Pantec), trade name "Thrasher" (manufactured by NIPPON COKE & ENGINEERING CO., LTD.), trade name "Trigonal Wet Milling Machine" (manufactured by Mitsui Miike Machinery), trade name "Cavitron" (manufactured by Eurotec), trade name "Milder" (manufactured by Pacific Machinery & Engineering Co., Ltd), or trade name "Fine Flow Mill" (manufactured by Pacific Machinery & Engineering Co., Ltd); a high-pressure emulsifier such as trade name "Microfluidizer" (manufactured by Mizuho Industrial), trade name "Nanomizer" (manufactured by NANOMIZER), or trade name "APV Gaulin" (manufactured by Gaulin); a membrane emulsifier such as trade name Membrane Emulsifier (manufactured by REICA Co., Ltd.); a vibration type emulsifier such as trade name "Vibro Mixer" (manufactured by REICA Co., Ltd.); and an ultrasonic emulsifier such as trade name "Ultrasonic Homogenizer" (manufactured by Branson). Note that, conditions for the emulsification operation using the emulsifying apparatus are not particularly limited. The conditions such as a treatment temperature, a treatment time, and the like may be appropriately selected so as to obtain a desired dispersion state.

In the production method (1) above, it is desirable to remove the organic solvent from the emulsion obtained through the emulsification operation.

The method of removing the organic solvent from the emulsion is preferably a method capable of reducing the content of the organic solvent (preferably an alicyclic hydrocarbon solvent) to 500 ppm by weight or less in the resulting synthetic polyisoprene latex. For example, methods such as vacuum distillation, atmospheric distillation, steam distillation, and centrifugation can be employed.

After removal of the organic solvent, to increase the solid content concentration of the synthetic polyisoprene latex, a concentration operation may optionally be carried out by a method such as vacuum distillation, atmospheric distillation, centrifugation, or membrane concentration. In particular, it is preferable to perform centrifugation from the viewpoint that the solid content concentration of the synthetic polyisoprene latex can be increased and the residual amount of the surfactant in the synthetic polyisoprene latex can be reduced.

It is preferable to carry out the centrifugation by, for example, using a continuous centrifugation machine, at a centrifugal force of preferably 100 to 10,000 G, a solid content concentration of the synthetic polyisoprene latex before centrifugation of preferably 2 to 15% by weight, a flow rate for feeding into the centrifugation machine of preferably 500 to 1700 kg/hr, and a back pressure (gauge pressure) of the centrifugation machine of preferably 0.03 to 1.6 MPa, from which a synthetic polyisoprene latex can be obtained as the light liquid after centrifugation. As a result, the residual amount of the surfactant in the synthetic polyisoprene latex can be reduced.

The solid content concentration of the synthetic polyisoprene latex used in the present invention is preferably 10 to 70% by weight, and more preferably 20 to 65% by weight. By setting the solid content concentration in the above range, the viscosity of the synthetic polyisoprene latex is more suitable, which facilitates transportation of the synthetic polyisoprene latex through piping and stirring in a blending tank.

The volume average particle size of the synthetic polyisoprene latex used in the present invention is preferably 0.1 to 10 µm, more preferably 0.5 to 3 µm, and even more preferably 0.5 to 2.0 µm. By setting the volume average particle diameter in the above range, the viscosity of the synthetic polyisoprene latex is more suitable, which facilitates transportation of the synthetic polyisoprene latex through piping and stirring in the blending tank. Such a volume average particle size also suppresses generation of a film on the latex surface when the synthetic polyisoprene latex is stored.

Further, in the synthetic polyisoprene latex, additives such as a pH adjuster, an antifoaming agent, a preservative, a crosslinking agent, a chelating agent, an oxygen scavenger, a dispersing agent, and an anti-aging agent, which are usually added in the latex field, may also be added.

Examples of the pH adjuster include: alkali metal hydroxides such as sodium hydroxide and potassium hydroxide; alkali metal carbonates such as sodium carbonate and potassium carbonate; alkali metal hydrogencarbonates such as sodium hydrogen carbonate; ammonia; organic amine compounds such as trimethylamine and triethanolamine; and the like. An alkali metal hydroxide or ammonia is preferable.

Styrene-Isoprene-Styrene Block Copolymer Latex

The styrene-isoprene-styrene block copolymer latex (SIS latex) used in the present invention is a latex of a block copolymer of styrene and isoprene (SIS) (wherein "S" stands for a styrene block and "I" stands for an isoprene block, respectively).

The production method of the SIS latex used in the present invention is not particularly limited, but a method in which the SIS latex is produced by emulsifying in water a solution or a fine suspension of SIS dissolved or finely dispersed in an organic solvent in the presence of a surfactant, and optionally removing the organic solvent is preferable.

The SIS can be obtained by a conventionally known method, for example, by block copolymerization of isoprene and styrene using a polymerization catalyst in an inert polymerization solvent. Further, the obtained SIS polymer solution may be used as is for producing the SIS latex, or may be used to produce the SIS latex by removing solid SIS from the polymer solution and then dissolving the solid SIS in an organic solvent.

At this time, impurities such as a residue of the polymerization catalyst remaining in the polymer solution after synthesis may be removed. In addition, an anti-aging agent (described later) may be added to the solution during or after the polymerization. Commercially available solid SIS can also be used.

Examples of the polymerization catalyst for obtaining the SIS include, but are not particularly limited to, trivalent and/or tetravalent transition metal compounds, such as a Ziegler type polymerization catalyst composed of trialkyl-aluminum-titanium tetrachloride; alkyllithium polymerization catalysts such as n-butyllithium and sec-butyllithium; and the like. Among these, from the viewpoint that the molecular structure control and productivity of the SIS, an alkyllithium polymerization catalyst is preferable.

As the organic solvent, the same organic solvents as described above for the synthetic polyisoprene can be used. Aromatic hydrocarbon solvents and alicyclic hydrocarbon solvents are preferable, and cyclohexane and toluene are particularly preferable.

The used amount of the organic solvent is, based on 100 parts by weight of the SIS, preferably 80 to 1,200 parts by weight, more preferably 100 to 1,150 parts by weight, and even more preferably 150 to 500 parts by weight.

Examples of the surfactant include the same surfactants as described above for the synthetic polyisoprene. Anionic surfactants are suitable, fatty acid salts, alkylbenzene sulfonates, alkyl sulfosuccinates, alkyl sulfates, and polyoxyethylene alkyl ether sulfates are preferable, fatty acid salts and alkylbenzene sulfonates are more preferable, fatty acid salts are even more preferable, and rosinates such as sodium rosinate and potassium rosinate are particularly preferable. When these anionic surfactants are used, the obtained synthetic polyisoprene latex contains an anionic surfactant. According to the present invention, by using a rosinate as the anionic surfactant, the obtained SIS latex contains a rosinate. In such a case, the rosinate acts as a pressure-sensitive adhesive, which enables the adhesive strength between the sheet base materials of the obtained packaging structure to be more suitable.

When the SIS latex contains a rosinate, the content ratio of the rosinate is, based on 100 parts by weight of the SIS, preferably 0.5 to 4 parts by weight, more preferably 0.8 to 4 parts by weight, and even more preferably 1 to 4 parts by weight. When the content ratio of the rosinate is within the above range, the adhesive strength between the sheet base materials of the obtained packaging structure can be made more suitable by the action of the rosinate as a pressure-sensitive adhesive.

The used amount of the surfactant is, based on 100 parts by weight of the SIS, preferably 0.1 to 50 parts by weight, and more preferably 0.5 to 30 parts by weight. If this amount is too small, the stability of the latex tends to deteriorate, and conversely if this amount is too much, foaming tends to occur and problems may occur during dip molding.

The amount of water used in the production method of the SIS latex described above is, based on 100 parts by weight of the organic solvent solution of the SIS, preferably 10 to 1,000 parts by weight, more preferably 30 to 500 parts by weight, and most preferably 50 to 100 parts by weight. Examples of the kind of water to be used include hard water, soft water, ion exchanged water, distilled water, zeolite water, and the like. Further, a polar solvent typified by an alcohol such as methanol may be used in combination with water.

Examples of the apparatus for emulsifying the organic solvent solution or fine suspension of SIS in water in the presence of a surfactant include the same apparatus described above for the synthetic polyisoprene. Further, the method of adding the surfactant is not particularly limited. The surfactant may be added in advance to either or both of an organic solvent solution or a fine suspension of water or SIS, or may be added to the emulsion during the emulsification operation, and may be added all at once or divided into several additions.

In the above-mentioned production method of the SIS latex, it is preferable to remove the organic solvent from the emulsion obtained through the emulsification operation to obtain the SIS latex. The method of removing the organic solvent from the emulsion is not particular limited, and methods such as vacuum distillation, atmospheric distillation, steam distillation, and centrifugation can be employed.

After removal of the organic solvent, to increase the solid content concentration of the SIS latex, a concentration operation may optionally be carried out by a method such as vacuum distillation, atmospheric distillation, centrifugation, or membrane concentration.

The solid content concentration of the SIS latex used in the present invention is preferably 10 to 70% by weight, and more preferably 20 to 65% by weight. By setting the solid content concentration in the above range, the viscosity of the SIS latex is more suitable, which facilitates transportation of the SIS latex through piping and stirring in a blending tank.

The weight average molecular weight of the SIS may be, in terms of standard polystyrene as determined by gel permeation chromatography analysis, 100,000 to 300,000, preferably 150,000 to 300,000, and more preferably 180,000 to 250,000. If the weight average molecular weight of the SIS is too large, the effect of an improvement in the adhesiveness of the SIS by a sterilization treatment (described later) is insufficient, and as a result, the adhesive strength between the sheet base materials of the obtained packaging structure is too low, and the sheet base materials may peel from each other. On the other hand, if the weight average molecular weight of the SIS is too small, the effect of an improvement in the adhesiveness of the SIS by the sterilization treatment (described later) becomes excessive, and as a result, the viscosity of the SIS becomes too high, so that when peeling the sheet base materials in order to remove the article to be packaged from the packaging structure, stringiness may be produced at the adhered portion between the sheet base materials.

The volume average particle size of the latex particles (SIS particles) in the SIS latex is preferably 0.1 to 10 μm, more preferably 0.5 to 3 μm, and even more preferably 0.5 to 2.0 μm. By setting the volume average particle diameter of the latex particles in the above range, the viscosity of the SIS latex is more suitable, which facilitates transportation of the SIS latex through piping and stirring in the blending tank. Such a volume average particle size also suppresses generation of a film on the latex surface when the SIS latex is stored.

The content of the styrene unit in the styrene block in the SIS included in the thus-obtained SIS latex is, based on all monomer units, preferably 70 to 100% by weight, more preferably 90 to 100% by weight, and even more preferably 100% by weight.

Further, the content of the isoprene unit in the isoprene block in the SIS is, based on all monomer units, preferably 70 to 100% by weight, more preferably 90 to 100% by weight, and even more preferably 100% by weight.

Note that, the content ratio of the styrene unit and the isoprene unit in the SIS is, in terms of the weight ratio of "styrene unit:isoprene unit", usually in the range of 1:99 to 90:10, preferably 3:97 to 70:30, more preferably 5:95 to 50:50, and even more preferably 10:90 to 30:70.

Further, in the SIS latex, additives such as a pH adjuster, an antifoaming agent, a preservative, a crosslinking agent, a chelating agent, an oxygen scavenger, a dispersing agent, and an anti-aging agent, which are usually added in the latex field, may also be added. Examples of the pH adjuster include the same pH adjusters described above for the synthetic polyisoprene. An alkali metal hydroxide or ammonia is preferable.

The synthetic polyisoprene latex and the SIS latex used in the present invention are obtained in the manner described above.

Next, the method of producing a packaging structure of the present invention will be described. The packaging structure of the present invention has a structure forming a package in which an article to be packaged is sandwiched by a first sheet base material and a second sheet base material, which are coated with the above-mentioned synthetic polyisoprene latex and/or SIS latex (hereinafter sometimes referred to as "polymer latex"). Specifically, in the packaging structure of the present invention, at least one of the first sheet base material and the second sheet base material is coated with the polymer latex. The article to be packaged is sandwiched by arranging the first sheet base material and the second sheet base material so as to oppose to each other via the surface coated with the polymer latex (latex coated surface). A portion where the first sheet base material and the second sheet base material are in contact with each other via their latex coated surfaces is pressed, which causes the first sheet base material and the second sheet base material to adhere to each other, thereby forming a structure packaging the article to be packaged. Note that, when both the first sheet base material and the second sheet base material are coated with the polymer latex, the first sheet base material and the second sheet base material can be adhered by bringing the latex coated surfaces famed on each of the first sheet base material and the second sheet base material into contact with each other and pressing the contact portion. Alternatively, if only one sheet base material is coated with the polymer latex, that one sheet base material and the other sheet base material can be adhered by bringing the other sheet base material (sheet base material not coated with the polymer latex) into contact with the latex coated surface famed on the one sheet base material, and pressing the contact portion.

In the following, as an example, a case will be described in which the article to be packaged is an adhesive plaster. However, the article to be packaged used in the present invention is not limited to an adhesive plaster. For example, the present invention may be applied in various kinds of article to be packaged for which sterilization is desirable, such as medical products other than an adhesive plaster.

Coating Step

The coating step in the production method of the present invention is a step of coating at least one surface of the first sheet base material and/or the second sheet base material with the polymer latex.

The first sheet base material and the second sheet base material have a function of preventing the article to be packaged, such as an adhesive plaster, from being contaminated by bacteria or the like by packaging the article to be packaged, such as an adhesive plaster.

Examples of the first sheet base material and the second sheet base material include, but are not limited to, paper materials such as glassine paper, high density polyethylene nonwoven fabric, polyolefin film, polyester film, and the like. Among these, a paper material is preferable, and glassine paper is particularly preferable, because such a material has excellent handleability (is suitably easy to fold) and is inexpensive.

The mass per unit area of the first sheet base material and the second sheet base material is preferably 20 to 300 g/m2, and more preferably 20 to 50 g/m$^2$.

The shape of the first sheet base material and the second sheet base material is not particularly limited, and it may be any shape as long as the article to be packaged, such as an adhesive plaster, can be packaged by the first sheet base material and the second sheet base material. Specifically, as the first sheet base material and the second sheet base material, a material having a shape larger than the adhesive plaster in both the length direction and the width direction can be used.

The shape of the first sheet base material and the second sheet base material may be the same or different from each other. In addition, the first sheet base material and the second sheet base material may be cut into an arbitrary shape after coating with the polymer latex.

The amount of the polymer latex for coating is not particularly limited, but in the case of coating both the first sheet base material and the second sheet base material, in terms of the weight after drying of the polymer latex used for coating, the amount used for coating is preferably 2 to 10 g/m$^2$, and more preferably 3 to 8 g/m$^2$. In the case of coating either one of the first sheet base material and the second sheet base material, in terms of the weight after drying of the polymer latex used for coating, the amount used for coating is preferably 4 to 20 g/m$^2$, and more preferably 6 to 16 g/m$^2$.

Either one of the sheet base materials of the first sheet base material and the second sheet base material may be coated with the polymer latex, and laminated. However, from the viewpoint of the adhesion between the base materials, it is preferable to coat both of the sheet base materials and laminate with the polymer latex. Further, it is preferable that the surface coated with the polymer latex is only one surface of the each of the sheet base materials.

The entire surface of the first sheet base material and the second sheet base material may be coated with the polymer latex, or only on a part of the first sheet base material and the second sheet base material may be coated therewith. In the case of coating a part of the first sheet base material and the second sheet base material with the polymer latex, in order to ensure that the adhesive plaster can be suitably packaged, when sandwiching the adhesive plaster between the first sheet base material and the second sheet base material, it is preferable to coat a position capable of surrounding the adhesive plaster with the polymer latex.

Note that, in the present invention, after the first sheet base material and the second sheet base material are coated with the polymer latex, a treatment for drying the polymer latex may be carried out. The drying temperature is not particularly limited, but is preferably 70 to 100° C., and more preferably 85 to 100° C. The drying time may be appropriately set according to the drying temperature, but it is preferably 3 to 30 minutes.

Lamination Step

The lamination step in the production method of the present invention is a step of sandwiching the article to be packaged, such as an adhesive plaster, between the first sheet base material and the second sheet base material in a state in which at least a part of the latex coated surface (surface coated with the polymer latex) of the first sheet base material and at least a part of the latex coated surface of the second sheet base material are in contact with each other to thereby obtain a laminated body.

Examples of the adhesive plaster include, but are not particularly limited to, an adhesive plaster composed of a surface base material, a pressure-sensitive adhesive layer provided on one surface of the surface base material, a pad layer provided on a part of the pressure-sensitive adhesive layer, a release sheet stuck so as to cover the surface on which the pad layer of the pressure-sensitive adhesive layer is provided, and optionally a print layer provided on the other surface of the surface base material.

Examples of the surface base material include, but are not particularly limited to, flexible films such as a polyurethane film, a vinyl chloride film, and a polyolefin film. Among these, a polyurethane film is preferable because of its excellent printability and high adaptability to curve surfaces.

The pressure-sensitive adhesive layer is a layer having a function for attaching the adhesive plaster to an affected part. Examples of the material constituting the pressure-sensitive adhesive layer include, but are not particularly limited to, acrylic pressure-sensitive adhesives, silicone pressure-sensitive adhesives, urethane pressure-sensitive adhesives, natural rubber, and the like.

The pad layer is a layer having functions such as hemostasis and protection of the affected part when the adhesive plaster is attached to the affected part. The material constituting the pad layer is not particularly limited, and for example a woven fabric or a nonwoven fabric, a polymer gel containing water or an oily component, and the like can be used. In addition, examples of the constituent material of the woven or nonwoven fabric include, but are not particularly limited to, rayon, polyethylene, polypropylene, polyolefin, alginate and the like. These may be used singly or in combination of two or more kinds.

The release sheet has a function of protecting the pressure-sensitive adhesive layer and the pad layer, and a function of preventing the adhesive plaster from adhering to the first sheet base material and the second sheet base material. This release sheet is not particularly limited, and a known release sheet can be used. However, from the viewpoint of preventing adhesion to the first sheet base material and the second sheet base material, a release sheet having a large surface roughness for the surface in contact with the first sheet base material or the second sheet base material is preferable. Examples of a release sheet having a large surface roughness are not particularly limited, but for example a release sheet obtained by coating a paper material with a release agent is preferable.

The printed layer, which is optionally provided on the surface base material, is, for example, a layer printed with a symbol such as a character. In the case of providing a printed layer on the surface base material, from the viewpoint of beautifying the printing finish, it is preferable to reduce the surface roughness of the surface on which the printed layer of the surface base material is provided.

In the lamination step, a laminated body is famed by sandwiching the article to be packaged, such as an adhesive plaster, between the first sheet base material and the second sheet base material such that at least a part of the latex coated surface of the first sheet base material and at least a part of the latex coated surface of the second sheet base material are in contact with each other. For example, the polymer (synthetic polyisoprene and/or SIS) constituting the polymer latex with which the first sheet base material is coated and the polymer (synthetic polyisoprene and/or SIS) constituting the polymer latex with which the second sheet base material is coated are brought into contact with each other, and the laminated body is famed by sandwiching an adhesive plaster by the first sheet base material and the second sheet base material such that a contact portion between the polymers surround the adhesive plaster. Specifically, the laminated body can be famed by, in a state in which the first sheet base material and the second sheet base material are in contact at both ends in the longitudinal direction and are in contact at both ends in the width direction, adhering the sheet base materials to each other while sandwiching the adhesive plaster. Note that, a non-adhered portion (in particular, in the case where an adhesive plaster is used as the article to be packaged, the portion which becomes the starting point for peeling when peeling the sheet base materials in order to remove the adhesive plaster) may be provided by, when adhering the first sheet base material and the second sheet base material, preventing a part in the length direction or in the width direction from adhering to each other.

Pressing Step

The pressing step in the production method of the present invention is a step of pressing a portion where at least the first sheet base material and the second sheet base material of the laminated body are in contact with each other at a temperature of 100° C. or less to thereby obtain a pressed laminated body.

The temperature at which the laminated body is pressed may be 100° C. or less, preferably 30 to 100° C., and more preferably 40 to 70° C. By setting the temperature at which the laminated body is pressed in the above range, deterioration of the article to be packaged, such as an adhesive plaster, due to heat can be suppressed, and materials with low heat resistance can be used as the first sheet base material and the second sheet base material.

The pressure when pressing the laminated body is not particularly limited, as long as the pressure is in a range capable of adhering the polymer constituting the polymer latex with which the first sheet base material is coated and the polymer constituting the polymer latex with which the second sheet base material is coated. This pressure may be appropriately set in accordance with the polymer constituting the polymer latex.

The pressing on the laminated body may be performed on the entire surface of the laminated body or on a part of the laminated body. However, from the viewpoint of that pressure can be more appropriately applied to the first sheet base material and the second sheet base material, it is preferable to press around the portion where the article to be packaged is housed, and to avoid pressing the portion containing the article to be packaged, such as an adhesive plaster of laminated body. Note that, when pressing on the laminated body, the above-mentioned non-adhered portion may be provided by not pressing a part in the length direction or the width direction of the first sheet base material and the second sheet base material.

Sterilizing Step

The sterilizing step in the production method of the present invention is a step of performing a sterilization treatment on the pressed laminated body. According to the present invention, a packaging structure can be obtained by performing a sterilization treatment on the pressed laminated body.

The sterilization treatment is not particularly limited, but a method of irradiating the pressed laminated body with radiation is preferable, and a method of irradiating the pressed laminated body with γ-rays is more preferable. By using a method of irradiating radiation as the sterilization treatment, in particular a method of irradiating γ-rays, the polymer (synthetic polyisoprene latex and/or SIS latex) on the first sheet base material and the second sheet base material constituting the pressed laminated body can be suitably oxidized, thereby improving the adhesiveness of the polymer and enabling the adhesive strength between the first sheet base material and the second sheet base material of the obtained packaging structure to be more suitable.

In particular, according to the present invention, as a result of such a sterilization treatment, the adhesiveness of the polymer can be improved, thereby enabling a more suitable adhesive strength between the first sheet base material and the second sheet base material, while on the other hand, it is possible to effectively prevent the first sheet base material and the second sheet base material from adhering with article to be packaged, such as an adhesive plaster. This allows the first sheet base material and the second sheet base material to be easily peeled from the article to be packaged when removing the article to be packaged from the packaging structure, while ensuring adhesive strength between the first sheet base material and the second sheet base material.

In the case of irradiating radiation on the pressed laminated body as a sterilization treatment, the entire pressed laminated body may be irradiated, or only a part of the pressed laminated body may be irradiated, but from the viewpoint that the article to be packaged, such as an adhesive plaster, in the pressed laminated body can be sterilized and a more suitable adhesive strength between the first sheet base material and the second sheet base material can be obtained as described above, it is preferable to irradiate the entire pressed laminated body.

Packaging Structure

The packaging structure of the present invention is famed obtained by the production method of the present invention described above, in which the article to be packaged is packaged by a first sheet base material and a second sheet base material coated with a polymer latex.

Since the packaging structure of the present invention is obtained by the production method of the present invention as described above, a suitable adhesive strength between the sheet base materials packaging the article to be packaged can be obtained by the sterilization treatment. This enables the occurrence of stringiness at the adhered portion between the sheet base materials to be effectively prevented when peeling the sheet base materials in order to remove the article to be packaged from the packaging structure, while ensuring the adhesive strength between the sheet base materials. Moreover, this also enables the sheet base materials to be easily peeled from article to be packaged. Therefore, the packaging structure of the present invention can be suitably used for packaging an article to be packaged requiring a sterilization treatment, such as a medical article like an adhesive plaster.

Further, the packaging structure of the present invention can effectively prevent the article to be packaged from causing allergic symptoms of immediate allergy (Type I) and delayed allergy (Type IV) in the human body. In other words, when a natural rubber latex is used for the packaging structure, when the article to be packaged in the obtained packaging structure comes into contact with the human body, proteins contained in the natural rubber may cause immediate allergy (Type I) symptoms in the human body. In addition, if a sulfur compound such as a sulfur vulcanizing agent or a sulfur vulcanization accelerator is added to the latex used for the packaging structure, when the article to be packaged in the obtained packaging structure comes into contact with the human body, the sulfur compound included in the latex may cause allergic symptoms of delayed type allergy (Type IV) in the human body.

In contrast, in the present invention, because a synthetic polyisoprene and/or styrene-isoprene-styrene block copolymer is used instead of natural rubber, and because there is no need to add a sulfur vulcanizing agent or sulfur vulcanization accelerator to the polymer latex, the occurrence of allergic symptoms of immediate allergy (Type I) and delayed allergy (Type IV) in the human body can be effectively prevented.

EXAMPLES

Hereinafter, the present invention will be described in detail by way of examples, but the present invention is not limited to these examples. In addition, unless stated otherwise, the tam "parts" is based on weight. The various physical properties were measured as follows.

Weight Average Molecular Weight (Mw)

A solution of synthetic polyisoprene or styrene-isoprene-styrene block copolymer in cyclohexane was diluted with tetrahydrofuran so that the solid content concentration was 0.1% by weight. Gel permeation chromatography analysis was pertained on this solution, and the weight average molecular weight (Mw) in tams of standard polystyrene was calculated.

Content of Anionic Surfactant 0.15 g of polymer latex was precisely weighed and added to 2 ml of ultrapure water, then acetonitrile was added to adjust the solution to 10 ml. Next, the supernatant was filtered through a disc filter having a pore size of 0.2 μm, and then measured using reversed-phase high performance liquid chromatography (HPLC) under the following conditions.

Column: Trade name "ZORBCX XDB-C18 1.8μ" (manufactured by Agilent Technologies)
Column temperature: 40° C.
Flow rate: 0.75 mi/min.
Detector: DAD (diode array detector)
Injection amount: 2 μL Peel Strength The packaging structures obtained in the examples and comparative examples were stored for one week at a temperature of 40° C. and a humidity of 75% RH. Next, after peeling the second sheet base material on the release sheet side of the adhesive plaster in the packaging structure, the release sheet was further peeled off, and a 25 μm-thick PET film cut it to the same width as the adhesive plaster was adhered to the pressure-sensitive adhesive layer of the adhesive plaster. Next, with the PET film in a fixed state, the first sheet base material was folded back and pulled in a 180-degree direction at a speed of 300 mm/min. The tensile stress at this time was measured and converted into N/25 mm (i.e., stress per 25 mm width of the adhered portion between the first sheet base material and the PET film), thereby obtaining the peel strength. Note that, the peel strength represents the adhesive strength of the first sheet base material when the packaging structure is stored in a high-temperature and high-humidity environment. It was determined that if the peel strength is in the range of 0.15 to 0.4 N/25 mm, the first sheet base material had a suitable adhesive strength even after storage in a high-temperature and high-humidity environment.

Stringiness and Adhesion

For the packaging structures obtained in the examples and comparative examples, when the adhered portion between the first sheet base material and the second sheet base material was peeled apart with the hand of a person, the presence/absence of stringiness of the peeled portion was visually observed, and the adhesion of the adhered portion between the first sheet base material and the second sheet base material was evaluated according to the following criteria.

A: The first sheet base material and the second sheet base material were very easily peeled apart.
B: The first sheet base material and the second sheet base material were adhered slightly, but were easily peeled apart.
C: The first sheet base material and the second sheet base material were strongly adhered, and were difficult to peel apart.
D: The first sheet base material and the second sheet base material were stuck together and could not be peeled apart. Alternatively, the first sheet base material or the second sheet base material was torn.
E: The first sheet base material and the second sheet base material were not adhered to each other in the first place.

Example 1

Production of Polymer Latex

A synthetic polyisoprene having a weight average molecular weight (Mw) of 4,000,000 prepared by solution polymerization using an organolithium catalyst as a polymerization catalyst was prepared. Subsequently, the prepared synthetic polyisoprene was dissolved in cyclohexane to prepare a solution of synthetic polyisoprene in cyclohexane.

Next, a mixed solution obtained by mixing 1250 parts of the solution of synthetic polyisoprene in cyclohexane (100 parts in terms of synthetic polyisoprene) and 1250 parts of an aqueous solution (surfactant aqueous solution) in which 10 parts of sodium dodecylbenzenesulfonate as an anionic surfactant had been dissolved was charged into a homogenizer and subjected to an emulsification dispersion treatment to obtain a synthetic polyisoprene emulsion. Then, the cyclohexane was distilled off from the synthetic polyisoprene emulsion, and the emulsion was further concentrated using a centrifugation machine to obtain a polymer latex of the synthetic polyisoprene. The solid content concentration of the obtained polymer latex was 59% by weight. The content of the anionic surfactant in the obtained polymer latex was measured in accordance with the above-mentioned method. The results are shown in Table 1.

Producing of Packaging Structure

First, glassine paper (40 g/m$^2$) was prepared. Then, the surface of the prepared glassine paper was coated with the above-mentioned polymer latex so that the amount used for coating after drying was 5 g/m$^2$. Next, the glassine paper coated with the polymer latex was dried at a temperature of 100° C. for 5 minutes, and then cut into equal sizes by a cutting machine. The size of the pieces of glassine paper after cutting was 28 mm in width and 88 mm in length. Then, of the pieces of glassine paper cut into equal sizes, one piece was taken as the first sheet base material coated with the polymer latex and the other was taken as the second sheet base material coated with the polymer latex.

Next, an adhesive plaster 20 mm in width and 70 mm in length and composed of a printed layer, a polyurethane sheet as a surface base material, a pressure-sensitive adhesive layer, a pad layer, and a release sheet, was prepared. Then, a laminated body was obtained by placing the adhesive plaster near the center of the first sheet base material, and bringing a part of the latex coated surface of the first sheet base material and a part of the latex coated surface of the second sheet base material into contact with each other so as to sandwich the adhesive plaster between the first sheet base material and the second sheet base material. Then, the edges of the first sheet base material and the second sheet base material were adhered by pressing them together at a temperature of 50° C. to obtain a pressed laminated body in which the adhesive plaster was sealed by the first sheet base material and the second sheet base material. The width (dimension of the portion where the first sheet base material and the second sheet base material were adhered in the width direction) of the adhered portion of the obtained pressed laminated body was as follows. First, at the portion where the adhesive plaster was not sandwiched in the width direction of the pressed laminated body, the width of the adhered portion was 28 mm, which was the same as the width of the first sheet base material (width of the second sheet base material). In addition, at the portion where the adhesive plaster was sandwiched in the width direction of the pressed laminated body, as a total of the adhered portions at both ends in the width direction of the pressed laminated body, the width of the adhered portion was 6 mm.

Next, a packing structure was obtained by performing a sterilization treatment on the pressed laminated body by irradiating the pressed laminated body with γ-rays at an irradiation dose of 30 kGy and irradiation time of 3 hours. The peel strength, stringiness, and adhesion of the obtained packaging structure were evaluated in accordance with the above-mentioned methods. The results are shown in Table 1.

Example 2

A polymer latex and a packaging structure were produced and evaluated in the same manner as in Example 1, except that synthetic polyisoprene having a weight average molecular weight (Mw) of 1,500,000 was used in place of the synthetic polyisoprene having a weight average molecular weight (Mw) of 4,000,000, and further, as the surfactant aqueous solution, an aqueous solution prepared by dissolving 10 parts of sodium dodecylbenzenesulfonate and 5 parts of sodium rosinate was used in place of the aqueous solution prepared by dissolving 10 parts of sodium dodecylbenzenesulfonate. The results are shown in Table 1.

Example 3

A polymer latex and a packaging structure were produced and evaluated in the same manner as in Example 2, except that for the anionic surfactant in the surfactant aqueous solution for producing the polymer latex, the used amount of sodium dodecylbenzenesulfonate was changed to 8 parts and sodium rosinate was not used. The results are shown in Table 1.

Example 4

A polymer latex and a packaging structure were produced and evaluated in the same manner as in Example 3, except that as the polymerization catalyst for producing the polymer latex, a Ti/Al Ziegler-Natta catalyst was used in place of the organolithium catalyst. The results are shown in Table 1.

Example 5

A polymer latex and a packaging structure were produced and evaluated in the same manner as in Example 4, except that as the anionic surfactant in the surfactant aqueous solution for producing the polymer latex, sodium rosinate was used in place of sodium dodecylbenzenesulfonate. The results are shown in Table 1.

Example 6

A polymer latex and a packaging structure were produced and evaluated in the same manner as in Example 3, except that a styrene-isoprene-styrene block copolymer having a weight average molecular weight (Mw) of 200,000 prepared by a solution polymerization method using an organolithium catalyst as a polymerization catalyst was used in place of the synthetic polyisoprene having a weight average molecular weight (Mw) of 1,500,000. The results are shown in Table 1.

Comparative Example 1

A polymer latex and a packaging structure were produced and evaluated in the same manner as in Example 5, except that a synthetic polyisoprene having a weight average molecular weight (Mw) of 6,000,000 was used in place of the synthetic polyisoprene having a weight average molecular weight (Mw) of 1,500,000. The results are shown in Table 1.

Comparative Example 2

A polymer latex and a packaging structure were produced and evaluated in the same manner as in Example 5, except that a synthetic polyisoprene having a weight average molecular weight (Mw) of 400,000 was used in place of the synthetic polyisoprene having a weight average molecular weight (Mw) of 1,500,000. The results are shown in Table 1.

Comparative Example 3

A polymer latex and a packaging structure were produced and evaluated in the same manner as in Example 5, except that a sterilization treatment was not carried out. The results are shown in Table 1.

Comparative Example 4

A polymer latex and a packaging structure were produced and evaluated in the same manner as in Example 5, except that a synthetic polyisoprene having a weight average molecular weight (Mw) of 6,000,000 was used in place of the synthetic polyisoprene having a weight average molecular weight (Mw) of 1,500,000, and the used amount of sodium rosinate as an anionic surfactant in the surfactant aqueous solution for producing the polymer latex was changed to 30 parts. The results are shown in Table 1.

[Table 1]

TABLE 1

| | Polymer | | | Polymer Latex |
|---|---|---|---|---|
| | Polymerization Catalyst Used in Polymerization | Polymer Type | Weight Average Molecular Weight (Mw) | Surfactant Used for Emulsification |
| Example 1 | organolithium catalyst | synthetic polyisoprene | 4,000,000 | sodium dodecylbenzenesulfonate |
| Example 2 | organolithium catalyst | synthetic polyisoprene | 1,500,000 | sodium dodecylbenzenesulfonate and sodium rosinate |
| Example 3 | organolithium catalyst | synthetic polyisoprene | 1,500,000 | sodium dodecylbenzenesulfonate |
| Example 4 | Ti/Al Ziegler-Natta catalyst | synthetic polyisoprene | 1,500,000 | sodium dodecylbenzenesulfonate |
| Example 5 | Ti/Al Ziegler-Natta catalyst | synthetic polyisoprene | 1,500,000 | sodium rosinate |
| Example 6 | organolithium catalyst | SIS | 200,000 | sodium dodecylbenzenesulfonate |
| Comparative Example 1 | Ti/Al Ziegler-Natta catalyst | synthetic polyisoprene | 6,000,000 | sodium rosinate |
| Comparative Example 2 | Ti/Al Ziegler-Natta catalyst | synthetic polyisoprene | 400,000 | sodium rosinate |
| Comparative Example 3 | Ti/Al Ziegler-Natta catalyst | synthetic polyisoprene | 1,500,000 | sodium rosinate |
| Comparative Example 4 | Ti/Al Ziegler-Natta catalyst | synthetic polyisoprene | 6,000,000 | sodium rosinate |

| | Polymer Latex Surfactant Content in Obtained Latex (parts by weight) | Sterilization treatment | Evaluation | | |
|---|---|---|---|---|---|
| | | | Peel Strength (N/25 mm) | Stringiness | Adhesion |
| Example 1 | 2.0 | yes | 0.18 | absent | A |
| Example 2 | 2.0 | yes | 0.25 | absent | A |
| Example 3 | 1.5 | yes | 0.28 | absent | A |
| Example 4 | 1.5 | yes | 0.31 | absent | A |

TABLE 1-continued

| | | | | | |
|---|---|---|---|---|---|
| Example 5 | 1.5 | yes | 0.34 | absent | A |
| Example 6 | 1.5 | yes | 0.24 | absent | A |
| Comparative Example 1 | 1.5 | yes | 0.08 | absent | E |
| Comparative Example 2 | 1.5 | yes | 0.25 | present | C |
| Comparative Example 3 | 1.5 | no | 0.09 | absent | E |
| Comparative Example 4 | 5.1 | yes | 0.56 | absent | D |

From Table 1, it can be seen that for the packaging structures obtained by performing a sterilization treatment on a pressed laminated body obtained using a pair of sheet base materials coated with a latex of a synthetic polyisoprene having a weight average molecular weight of 500,000 to 5,000,000 or a styrene-isoprene-styrene block copolymer having a weight average molecular weight of 100,000 to 300,000, the adhesion between the sheet base materials was suitable, stringiness did not occur, peel strength was in a good range, and therefore the adhesive force of the sheet base materials was maintained at a suitable level even when stored in a high-temperature and high-humidity environment (Examples 1 to 6).

On the other hand, for the packaging structure obtained using a pair of sheet base materials coated with a synthetic polyisoprene latex having a weight average molecular weight of more than 5,000,000, the sheet base materials did not adhere to each other, and the adhesive plaster could not be tightly sealed. Moreover, because the peel strength was low, the adhesive force of the sheet base materials when stored under a high-temperature and high-humidity environment was insufficient (Comparative Example 1).

Further, for the packaging structure obtained using a pair of sheet base materials coated with a synthetic polyisoprene latex having a weight average molecular weight of less than 500,000, the sheet base materials were adhered together too tightly, which made it difficult to peel them apart, and stringiness was continued when peeling the sheet base materials (Comparative Example 2).

For the packaging structure that did not undergo a sterilization treatment, the sheet base materials did not adhere together tightly, and the adhesive plaster could not be tightly sealed. Moreover, because the peel strength was low, the adhesive force of the sheet base materials when stored under a high-temperature and high-humidity environment was insufficient (Comparative Example 3).

In a packaging structure obtained using a pair of sheet base materials coated with a synthetic polyisoprene latex having a weight average molecular weight of more than 5,000,000, when the used amount of sodium rosinate used for production of the latex was increased to improve the adhesive strength between the sheet base materials due to the action of the sodium rosinate, the sheet base materials could not be peeled apart because they were too tightly adhered to each other. Moreover, because the peel strength was high, the adhesive force of the sheet base materials was too high even when stored under a high-temperature and high-humidity environment (Comparative Example 4).

The invention claimed is:

1. A method of producing a packaging structure, comprising:
    a coating step of coating at least one surface of a first sheet base material and/or a second sheet base material with a latex of a synthetic polyisoprene having a weight average molecular weight of 500,000 to 5,000,000 and/or a styrene-isoprene-styrene block copolymer having a weight average molecular weight of 100,000 to 300,000;
    a lamination step of sandwiching an article to be packaged between the first sheet base material and the second sheet base material in a state in which at least a part of the first sheet base material and at least a part of the second sheet base material are in contact with each other via the latex coated surface formed on the first sheet base material and/or the second sheet base material to thereby obtain a laminated body;
    a pressing step of pressing a portion where at least the first sheet base material and the second sheet base material of the laminated body are in contact with each other via the latex coated surface at a temperature of 100° C. or less to thereby obtain a pressed laminated body; and
    a sterilizing step of performing a sterilization treatment on the pressed laminated body.

2. The method of producing a packaging structure according to claim 1, wherein the latex contains a rosinate.

3. The method of producing a packaging structure according to claim 1, wherein the latex has a solid content concentration of 10 to 70% by weight.

4. The method of producing a packaging structure according to claim 1, wherein the article to be packaged is an adhesive plaster.

5. The method of producing a packaging structure according to claim 1, wherein the first sheet base material and/or the second sheet base material is a paper material.

6. The method of producing a packaging structure according to claim 1, wherein in the coating step, when coating both the first sheet base material and the second sheet base material with the latex, an amount of the latex for coating on the first sheet base material and the second sheet base material is, for each base material, 2 to 10 g/m$^2$ in terms of weight after drying.

* * * * *